(12) United States Patent
Sauer et al.

(10) Patent No.: US 11,596,562 B2
(45) Date of Patent: Mar. 7, 2023

(54) ABSORBENT ARTICLE WITH EXTENSIBLE EARS

(71) Applicant: The Procter & Gamble Company, Cincinnati, OH (US)

(72) Inventors: Andrew James Sauer, Cincinnati, OH (US); He Su, Beijing (CN); Erica Lynne Locke, Cincinnati, OH (US); Koichi Morimoto, Beijing (CN); Urmish Popatlal Dalal, Milford, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 820 days.

(21) Appl. No.: 16/163,662

(22) Filed: Oct. 18, 2018

(65) Prior Publication Data

US 2019/0125597 A1    May 2, 2019

(51) Int. Cl.
*A61F 13/56*    (2006.01)
*A61F 13/15*    (2006.01)
(Continued)

(52) U.S. Cl.
CPC .... *A61F 13/5622* (2013.01); *A61F 13/15203* (2013.01); *A61F 13/4902* (2013.01);
(Continued)

(58) Field of Classification Search
CPC .......... A61F 13/15203; A61F 13/49011; A61F 13/49015; A61F 13/4902; A61F 13/513; A61F 13/51456; A61F 13/5622; A61F 2013/15292; A61F 2013/1556; A61F 2013/49023; A61F 2013/49074; A61F 2013/49076
See application file for complete search history.

(56) References Cited

U.S. PATENT DOCUMENTS 3,848,594 A    11/1974  Buell
4,610,678 A    9/1986   Weisman
(Continued)

FOREIGN PATENT DOCUMENTS

JP    2003180737 A    7/2003
WO    WO9516746 A1    6/1995
(Continued)

OTHER PUBLICATIONS

International Search Report, PCT/CN2017/108476, dated Sep. 16, 2019, 10 pages.

*Primary Examiner* — Michele M Kidwell
(74) *Attorney, Agent, or Firm* — Sarah M. DeCristofaro; Wednesday G. Shipp

(57) ABSTRACT

An absorbent article has a liquid pervious topsheet, a liquid impervious backsheet, an absorbent core disposed between the topsheet and backsheet; first and second opposing longitudinal side edges, a front waist region and a back waist region; and a first and second back ear extending outwardly from the first and longitudinal side edges in the back waist region, respectively. The first and second back ears have an engineering strain greater than about 8% at about or below 2N of force when measured according to the Back Ear Extension Test, and a roughness Ra lower than about 300 μm when measured according to the Roughness Test.

22 Claims, 6 Drawing Sheets

(51) Int. Cl.
*A61F 13/513* (2006.01)
*A61F 13/514* (2006.01)
*A61F 13/49* (2006.01)

(52) U.S. Cl.
CPC .. *A61F 13/49011* (2013.01); *A61F 13/49015* (2013.01); *A61F 13/513* (2013.01); *A61F 13/51456* (2013.01); *A61F 2013/1556* (2013.01); *A61F 2013/15292* (2013.01); *A61F 2013/49023* (2013.01); *A61F 2013/49074* (2013.01); *A61F 2013/49076* (2013.01)

(56) References Cited

U.S. PATENT DOCUMENTS

| | | | |
|---|---|---|---|
| 4,662,875 A | 5/1987 | Hirotsu et al. | |
| 4,673,402 A | 6/1987 | Weisman et al. | |
| 4,699,622 A | 10/1987 | Toussant et al. | |
| 4,808,178 A | 2/1989 | Aziz et al. | |
| 4,834,735 A | 5/1989 | Alemany et al. | |
| 4,846,815 A | 7/1989 | Scripps | |
| 4,888,231 A | 12/1989 | Angstadt | |
| 4,894,060 A | 1/1990 | Nestegard | |
| 4,909,803 A | 3/1990 | Aziz et al. | |
| 3,860,003 A | 6/1990 | Buell | |
| 4,946,527 A | 8/1990 | Battrell | |
| 4,963,140 A | 10/1990 | Robertson et al. | |
| 5,137,537 A | 8/1992 | Herron et al. | |
| 5,147,345 A | 9/1992 | Young et al. | |
| 5,151,092 A | 9/1992 | Buell et al. | |
| 5,167,897 A | 12/1992 | Weber et al. | |
| 5,221,274 A | 6/1993 | Buell et al. | |
| 5,242,436 A | 9/1993 | Weil et al. | |
| 5,260,345 A | 11/1993 | DesMarais et al. | |
| 5,342,338 A | 8/1994 | Roe | |
| 5,387,207 A | 2/1995 | Dyer et al. | |
| 5,397,316 A | 3/1995 | LaVon et al. | |
| 5,499,978 A | 3/1996 | Buell et al. | |
| 5,507,736 A | 4/1996 | Clear et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,599,620 A * | 2/1997 | Huskey | A61F 13/58 428/343 |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,865,823 A | 2/1999 | Curro | |
| 5,993,432 A | 11/1999 | Lodge et al. | |
| 6,004,306 A | 12/1999 | Robles et al. | |
| 6,107,537 A | 8/2000 | Elder et al. | |
| 6,410,129 B2 | 6/2002 | Zhang et al. | |
| 6,432,098 B1 | 8/2002 | Kline et al. | |
| 6,677,258 B2 | 1/2004 | Carroll et al. | |
| 7,626,073 B2 | 12/2009 | Catalan | |
| 7,744,576 B2 | 6/2010 | Busam et al. | |
| 7,750,203 B2 | 7/2010 | Becker et al. | |
| 7,806,883 B2 | 10/2010 | Fossum et al. | |
| 7,819,853 B2 | 10/2010 | Desai et al. | |
| 8,618,350 B2 | 12/2013 | Mansfield | |
| 8,795,809 B2 | 8/2014 | Mansfield | |
| 8,835,709 B2 | 9/2014 | Isele et al. | |
| 9,289,332 B2 | 3/2016 | Wade et al. | |
| 9,301,888 B2 * | 4/2016 | Mansfield | A61F 13/565 |
| 2003/0135191 A1 * | 7/2003 | Price | A61F 13/496 604/391 |
| 2004/0006323 A1 * | 1/2004 | Hall | A61F 13/49014 604/385.24 |
| 2005/0215970 A1 * | 9/2005 | Kline | A61F 13/51474 604/385.22 |
| 2005/0215972 A1 * | 9/2005 | Roe | A61F 13/49015 604/385.29 |
| 2006/0161129 A1 * | 7/2006 | Zacharias | A61F 13/514 604/385.26 |
| 2007/0167929 A1 * | 7/2007 | Fossum | A61F 13/4902 604/385.3 |
| 2007/0249254 A1 | 10/2007 | Mansfield | |
| 2009/0258210 A1 | 10/2009 | Iyad et al. | |
| 2009/0264844 A1 | 10/2009 | Autran | |
| 2010/0228212 A1 * | 9/2010 | Desai | A61F 13/51484 604/367 |
| 2013/0082418 A1 | 4/2013 | Curro et al. | |
| 2013/0138072 A1 | 5/2013 | Morimoto et al. | |
| 2013/0231627 A1 | 9/2013 | O'Connell | |
| 2014/0257219 A1 * | 9/2014 | Neton | A61F 13/51401 604/365 |
| 2014/0257220 A1 * | 9/2014 | Neton | B32B 27/08 604/366 |
| 2014/0330233 A1 | 11/2014 | Schönbeck | |
| 2015/0322246 A1 * | 11/2015 | Broyles | B32B 27/22 428/141 |
| 2016/0129626 A1 * | 5/2016 | Arora | B32B 3/266 264/40.1 |
| 2016/0166445 A1 | 6/2016 | Miyamoto | |
| 2017/0087031 A1 | 3/2017 | Ottery et al. | |
| 2018/0021186 A1 | 1/2018 | Wågdahl | |
| 2018/0042778 A1 | 2/2018 | Lenser et al. | |
| 2018/0042780 A1 | 2/2018 | Lenser et al. | |
| 2018/0042785 A1 | 2/2018 | Dalal et al. | |
| 2018/0042787 A1 | 2/2018 | Lenser et al. | |
| 2018/0289851 A1 * | 10/2018 | Neton | B32B 27/12 |
| 2019/0374406 A1 * | 12/2019 | Morimoto | A61F 13/15699 |

FOREIGN PATENT DOCUMENTS

| | | |
|---|---|---|
| WO | WO0130289 A1 | 5/2001 |
| WO | WO2009073474 A2 | 6/2009 |
| WO | 2015191802 A1 | 12/2015 |
| WO | WO2018031842 A1 | 2/2018 |

* cited by examiner

ABSORBENT ARTICLE WITH EXTENSIBLE EARS

FIELD OF THE INVENTION

The present invention relates to absorbent articles having extensible ears.

BACKGROUND OF THE INVENTION

Absorbent articles are widely used to receive and store liquid contaminants for disposal. Commonly known absorbent articles include diapers, pull-on, pant-type diapers, adult incontinence articles, sanitary napkins, and panty liners. To effectively contain bodily exudates, the article should provide a snug fit around the waist and legs of a wearer.

It is not uncommon for absorbent articles to include elastic areas such as an elastic waist region and extensible ears to control the movement of liquids and provide a comfortable, conforming fit when the article is worn by a wearer.

Some absorbent articles such as diapers are manufactured to include back ears. For example, some varieties of diapers are manufactured with a pair of oppositely-oriented side back ears, extending laterally from each side of a back waist region of the diaper chassis, each back ear having a fastener located at or near the outboard edge thereof, and adapted to attach or adhere to a fastener receiving zone ("landing zone") disposed on a front waist region of the chassis. When the diaper is applied, back ears may traverse at least part of a high motion hip region of a wearer; therefore, extensible back ears are preferred over back ears without extensibility. Provision of extensibility on a diaper along a waist circumference using extensible back ears may be preferred as back ears are not constrained at application by a wearer laying on it while back waistband is. When the diaper is applied, each back ear may be in direct contact with the wearer's skin at a hip; therefore, extensible back ears having low roughness for being soft and gentle to the skin are preferred.

In some diapers, the back ears are formed at least in part of a laminate of one or more layers of nonwoven web and one or more layers or strands of a polymeric elastic material, and fashioned and adapted in such a way as to be elastically extensible in at least the direction in which the back ear is to be pulled during application and use. When worn, the back ears extend the diaper about the hip and waist of the wearer to anchor the diaper in use while still allowing the wearer to move comfortably. A fastening system is typically joined to the back ear to further secure the absorbent article about the wearer.

Elastic laminates suitable for extensible back ears may be produced by methods well known in the industry. For example, elastic laminates may be produced by joining one or more nonwoven layers and an elastic material at approximately zero relative strain where the nonwoven layer(s) and the elastic material may be bonded using adhesive. The nonwoven layer(s) and the elastic material may be bonded by one or more elastic layers being extruded directly on to at least one nonwoven layer.

There have been many absorbent articles employing high modulus back ears to maximize a sustained fit and minimize leakage of bodily exudates. High modulus back ears require users to use a relatively high force to extend the back ears and low force users may not be able to achieve a good sustained fit and minimal leakage with a product comprising high modulus back ears.

Some absorbent articles comprise back ears having low modulus stretch. Low modulus stretch may be achieved by utilizing strands of elastomeric material. Elastic strands may provide less elastomeric material per cross-sectional area of the back ear, and require less force to extend. Elastic strands when used to produce elastic materials such as stranded laminates, however, do not create a uniform and even surface. Additionally, stranded laminates may have large surface gathers due to its bonding structure. Non-uniform surfaces and large surface gathers may cause skin marking and irritation when worn by a wearer. Non-uniform surfaces and large surface gathers may also be perceived as the product using the material is less holistically designed or has lower quality.

Meanwhile, the presence of multiple components in an absorbent article may not be favored by users in view of holistic product perception.

Therefore, it is desirable to provide absorbent articles with back ears having an appropriately designed stretch engine for users to use the stretch during diaper application to achieve better fit and sizing.

It is also desirable to provide absorbent articles with back ears having a more even surface and reducing the risk of skin marking when worn by a wearer.

It is also desirable to provide absorbent articles having holistic integrated perception.

SUMMARY OF THE INVENTION

The present invention relates to an absorbent article comprising a liquid pervious topsheet, a liquid impervious backsheet, an absorbent core disposed between the topsheet and backsheet; a first and a second opposing longitudinal side edges, a front waist region and a back waist region; a first and second back ear extending outwardly from the first and longitudinal side edges in the back waist region, respectively; wherein each of the first and second back ears has an engineering strain greater than about 8% at about or below 2N of force when measured according to the Back Ear Extension Test, and wherein each of the first and second back ears have a roughness Ra lower than about 300 μm when measured according to the Roughness Test.

The present invention also relates to an absorbent article comprising a liquid pervious topsheet, a liquid impervious backsheet, an absorbent core disposed between the topsheet and backsheet; first and second opposing longitudinal side edges, a front waist region and a back waist region; a first and second back ear extending outwardly from the first and longitudinal side edges in the back waist region, respectively; wherein each of the first and second back ears has an engineering strain greater than about 8% at about or below 2N of force when measured according to the Back Ear Extension Test, and wherein each of the first and second back ears have about 1% to about 20% of a 4 hr growth when measured according to the 4 hr Growth Test.

BRIEF DESCRIPTION OF THE DRAWINGS

In the drawings, like numerals or other designations designate like features throughout the views.

DETAILED DESCRIPTION OF THE INVENTION

Figure 1A:
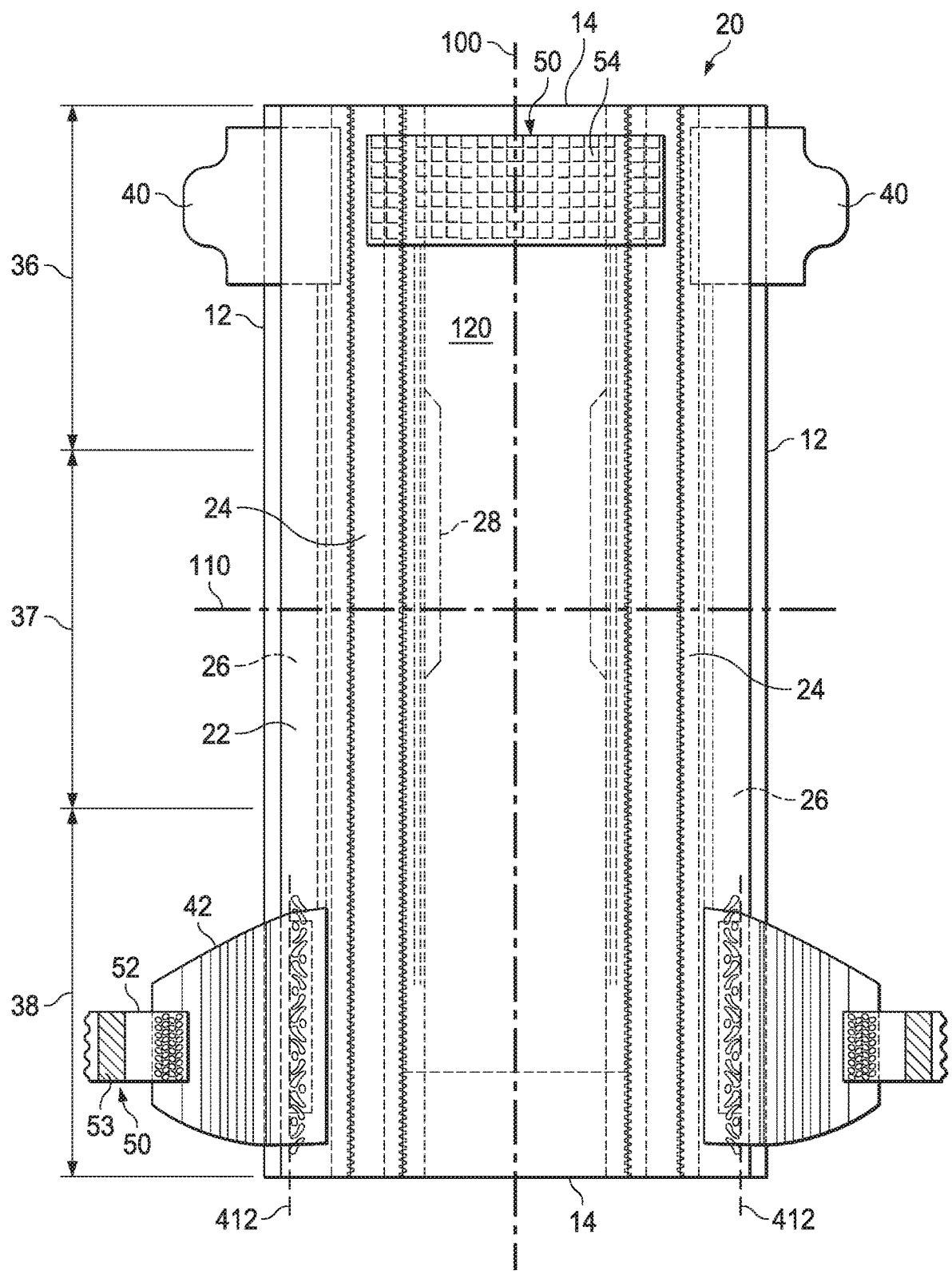
FIG. 1A is schematic plan view of an exemplary absorbent article according to the present invention.

Various non-limiting forms of the present disclosure will now be described to provide an overall understanding of the principles of the structure, function, manufacture, and use of an absorbent article comprising back ears having unique engineering strain properties and low surface roughness. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

As used herein, the term "absorbent article" refers to disposable devices such as infant, child, or adult diapers, adult incontinence products, training pants, sanitary napkins and the like which are placed against or in proximity to a body of a wearer to absorb and contain the various fluids (urine, menses, and/or runny BM) or bodily exudates (generally solid BM) discharged from the body. Typically, these absorbent articles comprise a topsheet, backsheet, an absorbent core, leg cuffs, optionally an acquisition system and/or a distribution system (which may be comprised of one or several layers), and typically other components, with the absorbent core normally placed at least partially between the backsheet and the acquisition and/or distribution system or between the topsheet and the backsheet. The absorbent articles comprising back ears having unique engineering strain properties and low surface roughness will be further illustrated in the below description and in the Figures in the form of one or more components of taped diaper. Nothing in this description should be, however, considered limiting the scope of the claims. As such the present disclosure applies to any suitable form of absorbent articles (e.g., diapers, training pants, adult incontinence products, sanitary napkins).

"Elastic," "elastomeric," and "elastically extensible" mean the ability of a material to stretch by at least 25% without rupture or breakage at a given load, and upon release of the load the elastic material or component exhibits at least 80% recovery (i.e., has less than 20% set).

As used herein, the term "extensible" refers to the property of a material, wherein: when a biasing force is applied to the material, the material can be extended to an elongated length of at least 110% of its original relaxed length (i.e. can extend 10%), without a rupture or breakage that renders the material unusable for its intended purpose. A material that does not meet this definition is considered inextensible. In some embodiments, an extensible material may be able to be extended to an elongated length of 125% or more of its original relaxed length without rupture or breakage that renders the material unusable for its intended purpose. An extensible material may or may not exhibit recovery after application of a biasing force.

As used herein, the term "film" means a sheet-like material wherein the length and width of the material far exceed the thickness of the material (e.g., 10×, 50×, or even 1000× or more). Films are typically liquid impermeable but may be configured to be breathable.

As used herein, "inboard", and forms thereof, with respect to features of a back ear, means furthest from or in a direction away from the free distal end.

As used herein, the term "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

Figure 1B:
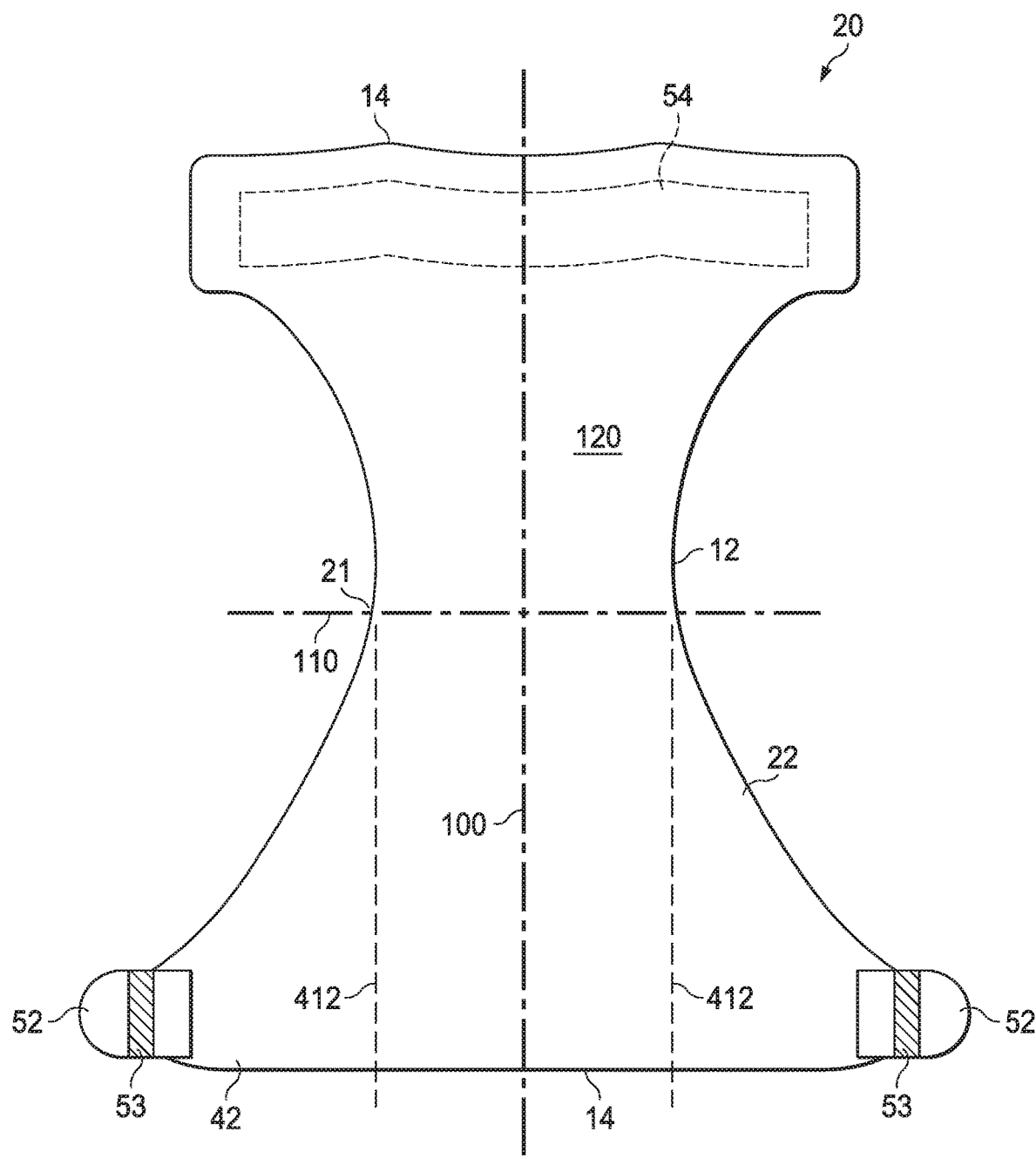
FIG. 1B is schematic plan view of another exemplary absorbent article according to the present invention.

As used herein, the term "Junction line," with respect to a back ear comprising components that are discrete from other components of an absorbent article, which back ear is welded, bonded, adhered or otherwise attached to the absorbent article, referring to FIG. 1A, means a longitudinal line 412, parallel with a longitudinal axis 100 of the absorbent article 20, through the outboard-most point in a chassis attachment bond 45 at which the back ear is bonded to the chassis. Note: In some examples of back ears, the back ear is bonded to the chassis to have an irregular shape or orientation; in such examples, the point at which such shape or orientation are closest to an outboard edge of the back ear will mark the location of the junction line. "Junction line," with respect to a back ear comprising one or more components that are not discrete from, but rather, integral with, one or more components of a diaper chassis that is disposed in an opened, extended position and laid flat and horizontally, viewed from above, referring to FIG. 1B, means a line 412 parallel to the longitudinal axis 100 through the edge of the chassis 22 at its narrowest point 21.

As used herein, the term "lateral" (and forms thereof), with respect to a line lying in a plane substantially occupied by an absorbent article back ear laid flat and horizontally, viewed from above, relates to a direction substantially perpendicular to a longitudinal axis of the absorbent article. "Lateral" and "width" (and forms thereof), with respect to features of an absorbent article back ear, relates to a direction, or generally following a direction, partially or entirely perpendicular to a longitudinal axis along the absorbent article. "Lateral" and "width" (and forms thereof), with respect to features of a diaper chassis, relates to a direction substantially parallel to the lateral axis of the chassis.

As used herein, the term "lateral axis" with respect to an absorbent article adapted to be worn by a wearer, means an axis perpendicular to the longitudinal axis, and equally dividing the longitudinal length of the article.

As used herein, the term "longitudinal" and "length" (and forms thereof), with respect to a line lying in a plane substantially occupied by an absorbent article back ear laid flat and horizontally, viewed from above, relates to a direction approximately aligned with the wearer's spine when the article would be normally worn, with the wearer in a standing or extended reclining position. "Longitudinal" and "length" (and forms thereof), with respect to features of a back ear, relates to a direction, or generally following a direction approximately aligned with the wearer's spine when the article would be normally worn, with the wearer in a standing or extended reclining position. "Longitudinal" and "length" (and forms thereof), with respect to features of a diaper chassis, relates to a direction approximately aligned with the wearer's spine when the article would be normally worn, with the wearer in a standing or extended reclining position.

As used herein, the term "longitudinal axis" with respect to an absorbent article adapted to be worn by a wearer, means an axis approximately aligned with the wearer's spine when the article would be normally worn, with the wearer in a standing or extended reclining position, and equally dividing the lateral width of the article, the lateral width being measured along a direction generally, parallel to the lateral axis.

As used herein, the term "nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

As used herein, the term "outboard", and forms thereof, with respect to features of a fastening member, means at or in a direction toward its free distal end.

Where features or elements of claims set forth herein are identified as "lines" or "line segments" or "points", such lines, line segments or points are not actual physical features themselves unless otherwise specified, but rather, are geometric references intended for use in describing locations on a physical structure.

Absorbent Article

Chassis

Referring to FIG. 1A, a diaper 20, an example of absorbent articles, comprises a chassis comprising a liquid pervious topsheet 24, a liquid impervious backsheet 26 and an absorbent core 28 disposed between the topsheet 24 and backsheet 26. The garment-facing surface 120 of the diaper 20 is facing the viewer. The diaper 20 includes a longitudinal centerline 100 and a lateral centerline 110. The diaper 20 includes a front waist region 36, a back waist region 38 opposed to the front waist region 36, and a crotch region 37 located between the front waist region 36 and the back waist region 38. The waist regions 36, 38 generally comprise those portions of the diaper 20 which, when worn, encircle the waist of the wearer. The waist regions 36 and 38 may include an elastic element that may gather or allow the material to extend in the front and/or back waist region 36, 38 about the waist of the wearer to provide improved fit and containment. The crotch region 37 is that portion of the diaper 20 which, when the diaper 20 is worn, is generally positioned between the legs of the wearer. The outer periphery of the diaper 20 is defined by longitudinal side edges 12 and end edges 14. The opposing longitudinal side edges 12 may be oriented generally parallel to the longitudinal centerline 100. Elastic elements may be disposed adjacent the side edges 12 of the diaper 20 to form gasket cuffs when the diaper 20 is in a fastened configuration.

The diaper 20 shown in FIG. 1A includes a liquid permeable topsheet 24, a liquid impermeable backsheet 26, and an absorbent core 28 disposed therebetween. The absorbent core 28 may have a body-facing surface and a garment facing-surface. The topsheet 24, the backsheet 26, and the absorbent core 28 may be assembled in a variety of well-known configurations. For example, the topsheet 24 may be joined to the core 28 and/or the backsheet 26. The backsheet 26 may be joined to the core 28 and/or the topsheet 24. It should be recognized that other structures, elements, or substrates may also be positioned in a joined or unjoined relationship between the core 28, the topsheet 24 and/or the backsheet 26. Nonlimiting examples of suitable diaper configurations are described generally in U.S. Pat. Nos. 3,860,003; 4,808,178; 4,909,803; 5,151,092; 5,221,274; 5,554,145; 5,569,234; 5,580,411; 6,004,306; and 7,626,073; and U.S. Publication No. 2007/0249254A.

The topsheet 24 typically includes a portion of the diaper 20 that is positioned at least in partial contact or close proximity to a wearer. Suitable topsheets 24 may be manufactured from a wide range of materials, such as porous foams; reticulated foams; apertured films; or woven or nonwoven web of natural fibers (e.g., wood or cotton fibers), synthetic fibers, or a combination of natural and synthetic fibers; or multilayer laminates of these materials. Generally, at least a portion of the topsheet 24 is liquid pervious, permitting liquid to readily penetrate through the thickness of the topsheet 24. Any portion of the topsheet 24 may be coated with a lotion as is known in the art. Examples of suitable lotions include those described in U.S. Pat. Nos. 5,607,760; 5,609,587; 5,635,191; and 5,643,588.

The absorbent core 28 may comprise a wide variety of liquid-absorbent materials commonly used in disposable diapers and other absorbent articles (e.g., superabsorbent polymer particles ("SAP") and/or airfelt). These materials may be combined to provide a core 28 in the form of one or more layers, which may include fluid handling layers such as acquisition layers, distribution layers and storage layers. Such absorbent cores 28 may also include layers to stabilize other core components. Such layers may include a core cover and a dusting layer. In certain embodiments, the absorbent core 28 may include less than 20 wt % of airfelt, based on weight of the absorbent core 28, or the absorbent core 28 may even be airfelt-free. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222; 7,750,203; and 7,744,576.

The backsheet 26 may be positioned such that it includes at least a portion of the garment-facing surface 120 of the diaper 20. The backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. One suitable backsheet 26 materials may include breathable materials that permit vapors to escape from the diaper 20 while still preventing exudates from passing through the backsheet 26. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

The backsheet 26 may also include more than one layer configured, for example, as discrete, unjoined layers or as laminate. It is to be appreciated that such laminate structures are not limited to the backsheet 26, but may be incorporated into any of the diaper 20 components described herein or commonly known in the art (e.g., ears or sides panels), as desired.

The diaper 20 may also include a fastening system 50. When fastened, the fastening system 50 typically interconnects the front waist region 36 and the back waist region 38 resulting in a waist circumference that generally encircles a wearer of the diaper 20. Exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

In certain embodiments, a portion of the fastening system 50 may be disposed on one or more ears, including for example front ears 40 disposed in the front waist regions and/or back ears 42 disposed in the back waist region. For example, the fastening system 50 exemplified in FIG. 1A, which includes a fastening member 52 and a landing zone 54, may be configured with the fastening member 52 disposed on the back ear 42. The fastening member 52 includes a fastener 53 that is engageable with a complementary receiving surface on the landing zone 54 and/or another portion of the diaper 20. In certain embodiments, the fastening member 52 may be an integral part of the back ear 42. When fastened, the fastening member 52 interconnects the front waist region 36 and the back waist region 38 resulting in a waist circumference that may encircle the wearer during wear of the absorbent diaper 20. The fastening member 52 may comprise a fastener 53 such as adhesives, hook and loop fastening components, interlocking fasteners such as tabs & slots, buckles, buttons, snaps, and/or hermaphroditic fastening components, although any other known fastening means are generally acceptable. An engagement element 53 also may include groups of separately identifiable fastening elements such as a plurality of discrete patches of adhesive-bearing material, discrete patches of hooks, etc.

The fastening system 50 may further comprise a landing zone to which a fastener can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening member 52 is foldable.

The fastening member 52 may be joined to any suitable portion of the diaper 20 by any suitable means. In some embodiments, the fastening member 52 is joined to the ear. The fastening member may be joined to the ear between layers. The fastening member may be joined to the ear on an exterior surface. In one nonlimiting example, the fastening member 52 and/or fastener 53 are mechanically bonded to the ear.

Back Ears

The diaper 20 may include one or more ears 40, 42, which extend laterally outwardly from one or both side edges 12 in the front and/or back waist regions 36, 38. Front ears 40 and/or back ears 42 may extend in the longitudinal direction from the end edge 14 of the diaper 20 to the portion of the side edge 12 of the diaper 20 that forms the leg openings when the diaper 20 is in a fastened configuration. The front ears 40 or the back ears 42 may be discrete components from other components of the diaper 20. For example, back ears 42 are welded, bonded, adhered or otherwise attached via a chassis attachment bond 45 to the diaper 20. The front ears 40 or the back ears 42 may be integral with a chassis component forming an extension thereof such that the front ears 40 or the back ears 42 may be configured as unitary elements of the backsheet, topsheet, core and/or another component in the chassis (i.e., they are formed from and are extensions of the backsheet, topsheet, core and/or the component materials), or the front ears 40 or the back ears 42 may be discrete component affixed to portions of chassis by any suitable means known in the art.

One or more of ears 40, 42, at least back ear 42, may be extensible or elastic. Ears 40 and/or 42 may be formed from one or more nonwoven webs, woven webs, knitted fabrics, polymeric and elastomeric films, apertured films, sponges, foams, scrims, elastic strands, elastic nonwovens or combinations and/or laminates of any the foregoing.

Figure 2:
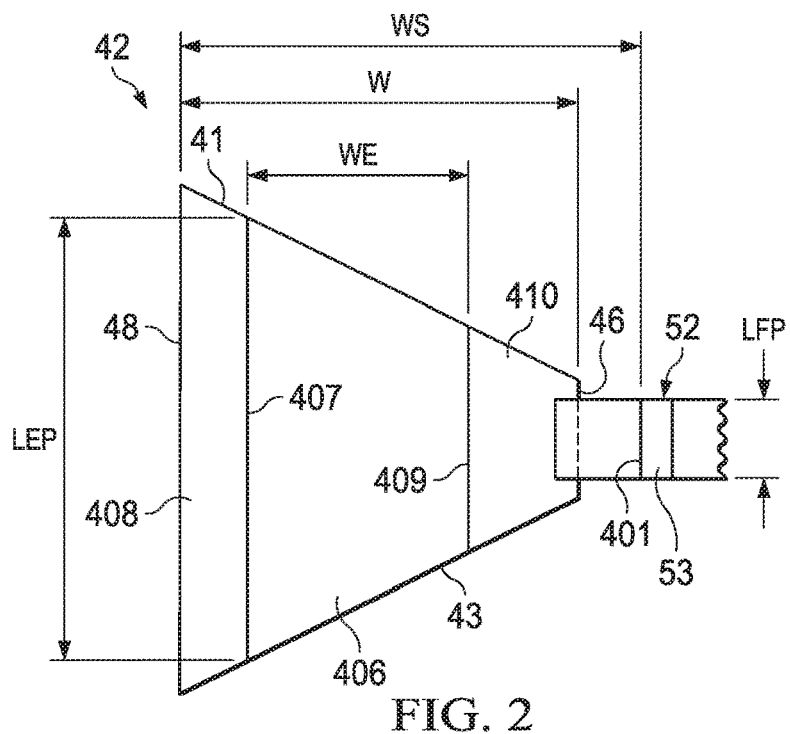
FIG. 2 is a schematic plan view of an exemplary ear for the present invention. The ear is shown in a flat, unextended state.

FIG. 2 illustrates a discrete back ear. Back ear 42 may include an outboard edge 46 and an inboard edge 48. The outboard edge 46 is the free distal longitudinal edge of the ear when said ear is joined to the chassis. The inboard edge 48 is substantially opposed to the outboard edge and is joined to or overlapped with the chassis when the ear is joined to the chassis. Ears may further include a first lateral edge 41 and an opposing second lateral edge 43.

In some embodiments, one or more of the ears 40, 42, especially back ear 42, may include an elastomeric material, such that the ear is extensible. In certain embodiments, back ear 42 may be formed of a stretch laminate such as a nonwoven/elastomeric material laminate or a nonwoven/elastomeric material/nonwoven laminate, which also results in the ear being extensible. Back ear 42 may be extensible laterally. In some embodiments, the back ear 42 is also extensible longitudinally.

Figure 3:
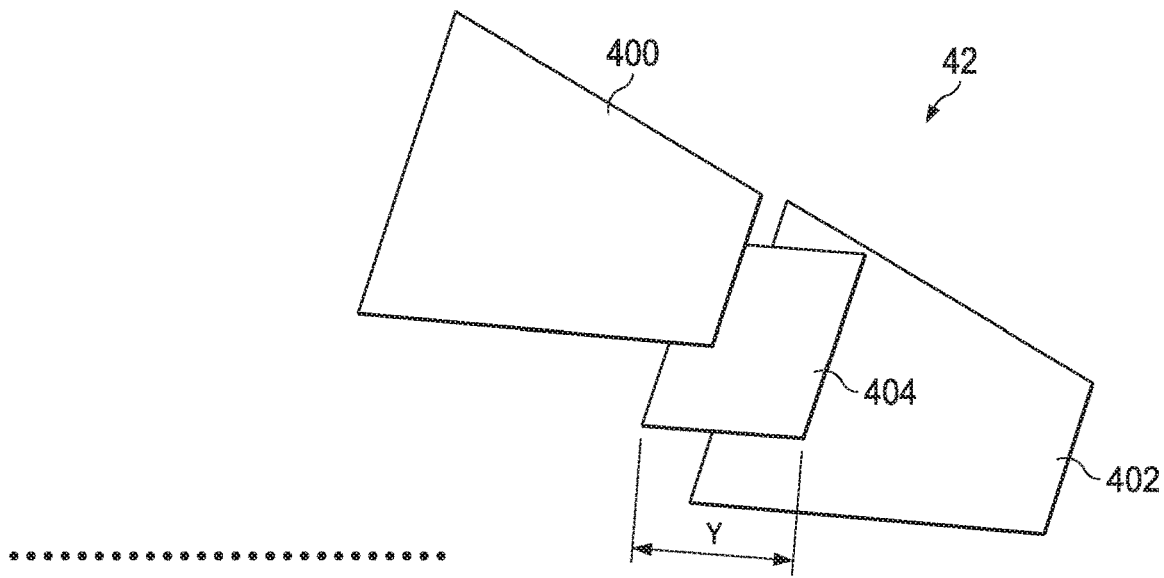
FIG. 3 is an exploded perspective view of an exemplary ear for the present invention.

In some embodiments, referring to FIG. 3, one or more of the ears 40, 42, especially back ear 42, comprises a first nonwoven layer 400, a second nonwoven layer 402 and an elastomeric layer 404. The elastomeric layer 404 may be sandwiched between the first and second nonwovens. The elastomeric layer 404 may be the same size as the first and second nonwoven layers 400, 402. The elastomeric layer 404 may be a smaller size than the first and second nonwoven layers 400, 402. The first nonwoven layer 400 may be formed by the same or different nonwoven material from the second nonwoven layer 402. The back ear may include at least one additional layer comprising, for example, nonwoven, an inelastic material, elastic or extensible material, etc.

Any suitable nonwoven may be used in one or more of the ears 40, 42. Suitable nonwoven webs can be formed by direct extrusion processes during which the fibers and webs are formed at about the same point in time, or by preformed fibers which can be laid into webs at a distinctly subsequent point in time. Example direct extrusion processes include but are not limited to: spunbonding, meltblowing, solvent spinning, electrospinning, and combinations thereof typically forming layers.

Example of nonwoven combination includes but are not limited to spunbond-meltblown-spunbond (SMS), spunbond-carded (SC), spunbond-airlaid (SA), meltblown-airlaid (MA), and combinations thereof, typically in layers. Combinations which include direct extrusion can be combined at about the same point in time as the direct extrusion process (e.g., spinform and coform for SA and MA), or at a subsequent point in time. In the above examples, one or more individual layers can be created by each process. For instance, SMS can mean a three layer, 'sms' web, a five layer 'ssmms' web, or any reasonable variation thereof wherein the lower case letters designate individual layers and the upper case letters designate the compilation of similar, adjacent layers. The fibers in a nonwoven web are typically joined to one or more adjacent fibers at some of the overlapping junctions. This includes joining fibers within each layer and joining fibers between layers when there is more than one layer. Fibers can be joined by mechanical entanglement, by chemical bond, ultrasonic bond, mechanical pressure bonds, thermal bonds, or adhesives or by combinations thereof.

In some embodiments, nonwoven fabric can be unbonded nonwoven webs, electrospun nonwoven webs, flashspun nonwoven webs (e.g., TYVEK™ by DuPont), or combinations thereof. These fabrics can comprise fibers of polyolefins such as polypropylene or polyethylene, polyesters, polyamides, polyurethanes, elastomers, rayon, cellulose, copolymers thereof, or blends thereof or mixtures thereof. The nonwoven fabrics can also comprise fibers that are homogenous structures or comprise bicomponent structures such as sheath/core, side-by-side, islands-in-the-sea, and other bicomponent configurations. For a detailed description of some nonwovens, see "Nonwoven Fabric Primer and Reference Sampler" by E. A. Vaughn, Association of the Nonwoven Fabrics Indus-3d Edition (1992).

In one approach, nonwoven web can be made of bi-component or multi-component fibers. One of the components of the fibers, preferably outer component, is soft polymer such as polyethylene or elastic polyolefin, polyurethane. For example, in sheath/core bi-component fiber, sheath can be made of polyethylene while core can be made of polypropylene.

In another approach, nonwoven web can be made of mono-component fiber. However, fiber is made of polymer blend to impart silky soft feel. For example, polypropylene nonwoven can be coarse. However, when blended with elastomeric polypropylene (VISTAMAXX® from Exxon), it can help improve the feel of the fiber.

In another approach, nonwoven web can be made of elastomeric polymer. For example, elastomeric polyolefins are used in fibers spinning and to make nonwoven web. Such webs have very sleek feel, and elastic properties, that is often desired for consumer products.

In another approach, additives can be added to polymer before spinning fiber. During fiber spinning and subsequent process steps to make nonwoven web, the additives migrate to fiber surface to provide silky feel. Amine and Amide based additives are commonly used up to 5% to impart softness.

In another approach, sleek chemical finish can be coated on the fibers or nonwoven webs. Chemical finishes based on oil, silicone, esters, fatty acids, surfactant etc. can be employed. Softeners such as anionic, cationic or nonionic can also be used to improve drape, and touch. Various coating techniques, like roll coating, screen coating, gravure coating, slot coating, spray coating, can be used to apply finish.

In another approach, nonwoven fiber diameter can be reduced to produce fine fibers and to provide silk like feel. Meltblown fiber is one technology to reduce fiber diameter to less than 20 microns. Alternatively, nanofibers, having a diameter of less than 1 micron, made from a melt film fibrillation process with a polymer composition disclosed in U.S. Pat. No. 8,835,709 patent can be used to provide softness.

In nonlimiting examples, a nonwoven comprises a meltblown layer. Additionally or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens in the ear may be void of meltblown layers. While meltblown layers have been found to enhance bonding in ears requiring adhesive (given the meltblown layer's inhibition of the adhesive's diffusion through the porous nonwoven structure), meltblown layers often lack strength. In some embodiments, a nonwoven consists essentially of spunbond layers. In some nonlimiting examples, both the first and the second nonwoven comprises at least 2 spunbond layers, or 3 or more spunbond layers.

Where one or more of the ears 40, 42 comprise more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

The elastomeric layer 404 comprises one or more elastomeric materials which provide elasticity to at least a portion of the layer 404. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, elastic strands, scrims, and the like. Elastomeric materials can be formed from elastomeric polymers including polymers comprising styrene derivatives, polyesters, polyurethanes, polyether amides, polyolefins, polyvinyl chloride, combinations thereof or any suitable known elastomers. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, USA), HYTREL (polyester; available from DuPont, USA), VISTAMAXX (homopolyolefins and random copolymers, and blends of random copolymers, available from EXXON Mobile, USA), and VERSIFY (homopolyolefins and random copolymers, and blends of random copolymers, available from Dow Chemical Company, USA).

In nonlimiting examples, the elastomeric layer 404 comprises a film. The film may comprise a single layer or multiple layers. The film may be elastic in the lateral direction. The elastomeric layer 404 may comprise a width, Y, as shown for example in FIGS. 2 and 3. In some embodiments, Y is less than the width, W, of the back ear 42 by at least about 10 mm. The elastomeric layer 404 may have a longitudinal dimension that is the same as the back ear 42 along with the width Y of the elastomeric layer 404, or a longitudinal dimension that is less than the longitudinal length of the ear at any point along with the width of the elastomeric layer. In some embodiments, the elastomeric layer may have a basis weight of from about 5 to about 150 gsm, or from about 10 to about 100 gsm, or less than about 150 gsm, reciting for each range every 5 gsm increment therein.

As also illustrated in FIGS. 2 and 3, the back ear 42 comprises an elastic region 406. The elastic region 406 is generally defined by the perimeter of an area elastically extensible in the elastomeric layer 404. In case the elastomeric layer 404 has an inextensible area at any edge in the width direction, the width, WE, of the elastic region 406 is shorter than the width, Y, of the elastomeric layer 404. In some embodiments, the area of the elastic region comprises at least about 20% of, or from about 30% to about 100% of the total area of the ear, reciting for said range every 5% increment therein. In further embodiments, Y (i.e., the maximum width of the elastomeric layer 404) is at least about 20% of, or from about 25% to about 85%, or from about 35% to about 100% of the total width, W, of the back ear 42, reciting for each range every 5% increment therein. The back ear 42 may further comprise one or more inelastic regions. In certain embodiments, the back ear 42 comprises a first inelastic region 408, which extends laterally outward from the inboard edge 48 and is adjacent to the elastic region 406 at an inboard edge 407 of the elastic region 406. The ear may further include a second inelastic region 410, which may extend laterally inward from the outboard edge 46 and may be adjacent to outboard edge 409 of the elastic region 406. The first and second inelastic regions may be made of the same material(s) or different materials. Referring to FIG. 2, the length of a fastener 53 inboard edge is shown as LFP, and the length of an inboard edge 407 of the elastic region 406 is shown as LEP. In an embodiment wherein an back ear 42 has an elastic region 406 with no inelastic region, LEP is the length of inboard edge 48 of the back ear 42.

Still referring to FIG. 2, a reference width WS can be identified, as the width from the junction line 412 to an inboard edge 401 of the fastener 53. In some examples, the fastener 53 may have an irregular shape or orientation, or consist of a plurality of engaging portions; in such examples, the point at which such shape, orientation or extensible portions are closest to a longitudinal axis of an absorbent article is considered the inboard edge 401 of the fastener 53.

In certain embodiments, the back ear 42 comprises a laminate comprising multiple layers, wherein one of the layers is strained to a greater degree than a remaining layer during lamination. In this way, the less extensible layer, the nonwoven 400, 402 in case of FIG. 3, will form gathers when the laminate is in a relaxed state. In some embodiments, the elastomeric layer is strained while the nonwoven(s) are in a relaxed state during lamination. The elastomeric layer may be stretched one or more directions. Corrugations then may form in the nonwoven layer(s) when the subsequently formed laminate is in a relaxed state. Non-limiting examples of the laminating suitable for the present invention include an extrusion bonded laminate and an ultrasonically bonded laminate. Extrusion bonded laminates may be produced according to a conventional extrusion bonded laminate production process by extruding a molten film directly on to a carrier such as a nonwoven. An ultrasonically bonded laminate may be produced by the process and/or equipment disclosed in U.S. Patent App. No. 62/374,010. It is to be appreciated that ultrasonically bonded elastic laminates may include various portions of components bonded together in various ways and with bonds having differing or identical bond patterns. Non-limiting examples of ultrasonically bonded laminates comprising a bond pattern include those disclosed in U.S. patent application Ser. No. 15/674,561 filed on Aug. 11, 2017 or an equivalent PCT application No. US2017/46398 filed on Aug. 11, 2017.

A laminate useful for the present invention may further comprise a reinforcement layer to improve strength of the laminate. Non-limiting examples of such laminates are disclosed in U.S. patent application Ser. No. 15/674,575 filed on Aug. 11, 2017 or an equivalent PCT application No. US2017/46393 filed on Aug. 11, 2017.

In certain embodiments, the laminate useful for the present invention is produced without using glue. Laminates with substantially no glue may be preferable with respect to lower potential malodor issue, production cost, process complexity and process contamination with glue. In other embodiments, the laminate for the present invention is a non-activated laminate produced without conducting a laminate activation step. "Activated" or "activation", when used relative a laminate for a back ear herein, means the mechanical deformation of a plastically extensible laminate that results in permanent elongation of the laminate, in the direction of activation in the X-Y plane of the laminate. For example, activation occurs when a laminate is subjected to a stress that causes the laminate to strain beyond the onset of plasticity, which may or may not include complete mechanical failure of the laminate or a portion of laminate. Activation of a laminate that includes an elastic material joined to a plastically extensible material typically results in permanent deformation of the plastic material, while the elastic material returns substantially to its original dimension. Activation processes include incremental stretching and SELFing. "Incremental stretching" means a process in which a web material is controllably plastically stretched in increments along one or more directions by being passed under tension between the surfaces of a pair of stretching members having continuously intermeshing ridges and valleys, or other intermeshing features as described for example, in U.S. Pat. Pub. No. 2013/0082418 and U.S. Pat. No. 5,167,897. Ring-rolling is a type of incremental stretching. "SELF" or "structured elastic-like film" means a process in which a web material is controllably plastically stretched in increments along one or more directions by being passed under tension between the surfaces of a pair of stretching members having discontinuously intermeshing ridges and valleys, or other features as described in, for example, U.S. Pat. No. 5,993,432.

In another method, elastic laminates may be consolidated or pre-contracted laminates where an elastic material is strained prior to being bonded to a nonwoven layer. The elastic material, for example when it is film may be pre-activated before being laminated with nonwoven layer(s) to create a plurality of cracks and tears in the skins at a microscopic scale. In turn, these cracks and tears may help reduce the skin contribution to the extension forces. Pre-activation of film may be performed by for example, a process disclosed in U.S. patent application Ser. No. 15/674, 625 filed on Aug. 11, 2017 equivalent to PCT application No. US2017/46397 filed on Aug. 11, 2017.

In nonlimiting examples, the elastomeric layer is stretched in a direction corresponding with the lateral direction of the article. In other words, when the ear is joined to the chassis subsequent to lamination, the ear laminate will be oriented such that the ear is stretchable in the lateral direction of the article. In further nonlimiting examples, the ear is also stretchable in the longitudinal direction.

Back ear 42 may be attached to an absorbent article in any suitable manner, including, but not limited to, continuous or intermittent adhesive bonding, compression bonding, heat bonding, ultrasonic bonding, etc.

Back ears in absorbent articles according to the present invention have an engineering strain equal to or greater than about 8%, or greater than about 10% at about or below 2N of force when measured according to the Back Ear Extension Test. It was noticed that some users tend not to fully utilize the extension property of the back ear which results in poor sustained fit and a potential leakage problem. An engineering strain at about or below 2N may be meaningful as 2N is considered an average force some users initially apply on diaper when the users apply diapers on wearers. When the back ears have an engineering strain lower than 8% at about or below 2N, users may perceive the back ears do not provide enough extensibility. In some embodiments, a back ear extends at least about 10 mm at about or below 2N of force measured according to the Back Ear Extension Test described later. The at least about 10 mm extensibility at about or below 2N may communicate noticeable extensibility of the back ear.

Back ears in absorbent articles according to the present invention have an engineering strain less than about 50%, or less than about 40% at about or below 4N of force when measured according to the Back Ear Extension Test described later. If the force to extend a back ear does not increase sufficiently such that the back ear extends more than about 50% at about or below 4N, users may perceive the absorbent article is low quality, or that the back ears are weak and may break during use. Additionally, back ears that extend more than about 50% at about or below 4N may lead to poor sustained fit, increased sagging, and leakage. An engineering strain at about or above 4N may be meaningful as 4N is considered almost the maximum force some users apply on diaper when the users apply diapers on wearers.

Back ears in absorbent articles according to the present invention have a roughness Ra equal to or lower than about 300 μm, equal to or lower than about 150 μm, or equal to or lower than about 100 μm when measured according to the Roughness Test. When the roughness of a back ear is higher than about 300 μm, it may be perceived or felt the back ear is harsh and is not gentle to the skin.

Back ears in absorbent articles according to the present invention may have a 4 hr growth in the range of about 1% to about 20%, or about 1% to about 10%, or about 1% to about 5% when measured according to the 4 hr Growth Test. When the 4 hr growth (%) of a back ear is lower than 20%, 10% or lower than 5%, the diaper having the back ears may be less prone to slip or sag about a wearer.

For the purposes of providing holistic material integrity, the back ears in use status may have about 70% of opacity, or about 75% of opacity.

As noted in the Background, back ears of a diaper may be designed and situated to wrap around a wearer's hips. As a result, they may be in contact with the skin at the wearer's hips while the diaper is being worn. Additionally, while a diaper is being worn the back ears will sustain and transfer varying tension forces, particularly when the wearer is active and bending at the hips. These tension forces have normal force components acting on the wearer's skin. Thus, it may be desirable that the material forming the skin-contacting portions of a back ear 42 be selected with the objectives of appropriately designed extensibility, pliability and an even surface area. Increasing these variables generally may help to provide for sustained fit, improve undesired sag and/or leakage of bodily exudates, and reduce the likelihood of skin marking and chafing.

Test Method

Preparation of Back Ear Specimens

1. Open a diaper.
2. If the back ear is attached to an article, cut it free from the article at a location sufficiently inboard of the junction line so that a tensile tester's grip can sufficiently grasp the specimen for the testing beyond the junction line. If the back ear is an integral part of a chassis, identify the junction line and mark a line on the back ear coincident with the junction line, and cut it free from the article at a location sufficiently inboard of the junction line so that a tensile tester's grip can sufficiently grasp the specimen for the testing beyond the junction line. For Back Ear Extension Test, continue steps 3-4 below.
3. Lay the back ear on a substantially flat, horizontal surface and measure width WS as described herein, with no lateral tension force applied to the back ear.
4. Measure lengths LFP and LEP as described herein to the nearest 1 mm, with a steel ruler traceable to NIST or an equivalent.
5. Mark a midpoint of LFP. The midpoint is at ½ of LFP.

Back Ear Extension Test

An engineering strain and an extension of a back ear specimen is measured using a constant rate of extension tensile tester with computer interface such as MTS Alliance under Test Works 4 software (MTS Systems Corp., USA) fitted with a suitable load cell. The load cell should be selected to operate within 10% and 90% of its stated maximum load. All testing is performed in a conditioned room maintained at about 23° C.±2° C. and about 50%±2% relative humidity. Herein, width and length of the specimen are a lateral width and longitudinal length as defined herein. Precondition specimens at about 23° C.±2° C. and about 50%±2% relative humidity for 2 hours prior to testing.

1. Insert the outboard edge of the back ear including a fastener into the upper clamp in the tester such that the clamp is centered in the tensile tester fixture, and engage the clamp to grip the specimen. The clamp width is at least as wide as the length of an inboard edge of the fastener, and preferably is not wider more than 1 inch than the length of an inboard edge of the fastener. The face of the clamp (once it grips the specimen) is aligned with the inboard edge of the fastener to within 1 mm, the longitudinal midpoint of LFP is aligned with the center of the clamp, and the unclamped portion of the back ear hangs freely downward from the upper clamp.
2. Insert the inboard edge of the back ear into the lower clamp in the tensile tester. The lower clamp width is chosen such that no portion of the back ear extends beyond the width of the clamp, and preferably the lower clamp width is not wider more than 1 inch than the length of the portion of the back ear inserted into the clamp. The face of the clamp (once it grips the specimen) is aligned with the junction line 412 to within 1 mm, and the specimen is oriented such that if a lateral line perpendicular to a longitudinal axis of the diaper having the back ear were drawn from the midpoint of LFP, it would extend vertically and align with the center of the fixture holding the lower clamp.
3. Extend the jaws of the tensile tester such that the distance between the face of the upper clamp and face of the lower clamp is equal to WS. Set gage length equal to WS.
4. Zero the crosshead location and load, and engage the lower clamp to grip the specimen.
5. Set the tensile tester to extend the specimen at a rate of 254 mm/minute and collect data at a frequency of at least 100 hz.
6. Initiate the test such that the tensile tester's clamp extends the specimen at the defined rate and data including extension and load is collected into a data file.
7. Measure an extension, a distance extended from a zero-point, under load at 2N, and determine an engineering strain under load at 2N, calculated as $$100\% \times [\text{extension at } 2N \text{ load}/WS \text{ (at no lateral tension load)}].$$

8. Measure an extension under load at 4N, and determine an engineering strain under load at 4N, calculated as 100%×[extension at 4N load/WS (at no lateral tension load)].

9. In like fashion, a total of three (3) replicate samples are tested for each test product to be evaluated. Report the extension as the mean of the replicates to the nearest 0.1 cm, and engineering strain as the mean of the replicates to the nearest 0.1 unit.

4 hr Growth Test

A 4 hr growth of a back ear specimen is measured using a clamp affixed to a vertical stand, and an appropriate weight to deliver a total of 408+/−1 grams on the back ear specimen. The vertical stand and weight are configured such that when a back ear specimen is attached for testing, the back ear specimen can at least double in length, or at least increase in length by 100 mm (whichever is larger) without the weight contacting the table, floor, or base of the stand.

Figure 5A:
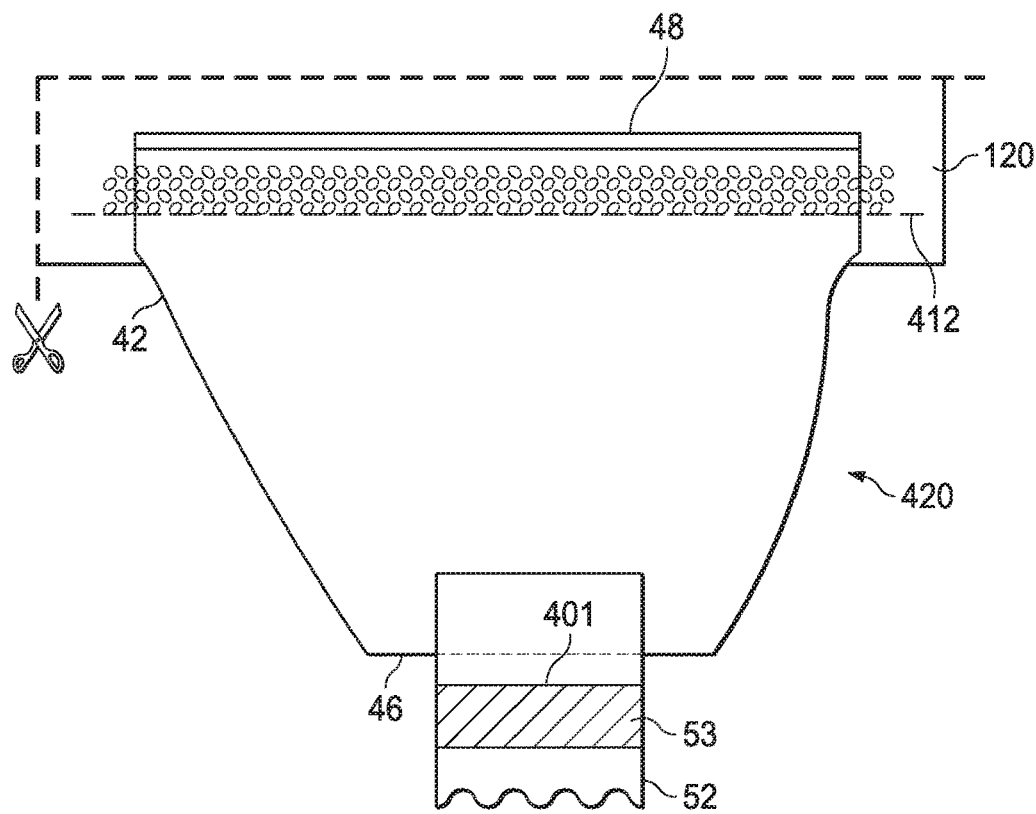
FIGS. 5A-5D are plan views of the Roughness Test.

1. Prepare a back ear specimen referring to Preparation of Back Ear Specimens above and FIG. 5A.

2. Insert the outboard edge of the back ear specimen including a fastener into the clamp on the vertical stand such that the back ear specimen is centered with the vertical stand, and engage the clamp to grip the specimen. The clamp width is at least as wide as the length of an inboard edge of the fastener, and preferably is not wider than 1 inch more than the length of an inboard edge of the fastener. The face of the clamp (once it grips the specimen) is aligned with the inboard edge of the fastener to within 1 mm, the longitudinal midpoint of LFP is aligned with the center of the clamp, and the unclamped portion of the back ear hangs freely downward from the clamp.

3. Record the distance from the inboard edge of the fastener to the junction line as the back ear width.

4. Attach the weight to the inboard edge of the back ear using a clamp. The clamp width is chosen such that no portion of the back ear extends beyond the width of the clamp, and preferably the clamp width is not wider than 1 inch more than the length of the portion of the back ear inserted into the clamp. The face of the clamp (once it grips the specimen) is aligned with the junction line to within 1 mm, and the specimen is oriented such that if a lateral line were drawn from the midpoint of LFP, it would extend vertically and align with the center of the clamp. The clamp and weight together should be chosen to apply 408+/−1 grams on the back ear specimen. The weight must be hanging free and unobstructed without resting on any object.

5. Within 5 seconds of attaching the weight and releasing it to hang from the back ear, record the distance from the inboard edge of the fastener to the junction line as Extension at Time 0.

6. Allow the back ear specimen to sit undisturbed for 4 hours. After 4 hours, measure the distance from the inboard edge of the fastener to the junction line as Extension at 4 hr.

7. Repeat steps 1-6 for 5 back ear specimens. Calculate 4 hr Growth=Average ([Extension at 4 hr]−[Extension at Time 0])

8. Calculate 4 hr Growth (%)=Average (([Extension at 4 hr]−[Extension at Time 0])/[Back Ear Width]×100)

Roughness Test

1. Prepare a back ear specimen referring to steps 1 and 2 in the Preparation of Back Ear Specimens above and FIG. 5A.

Figure 5C:
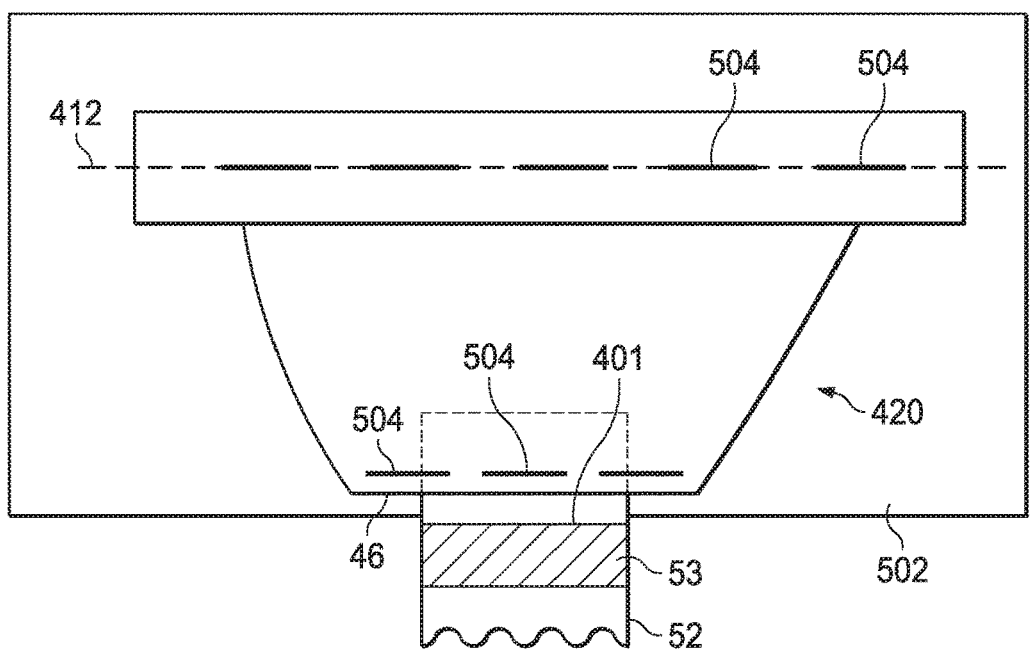
Figure 5B:
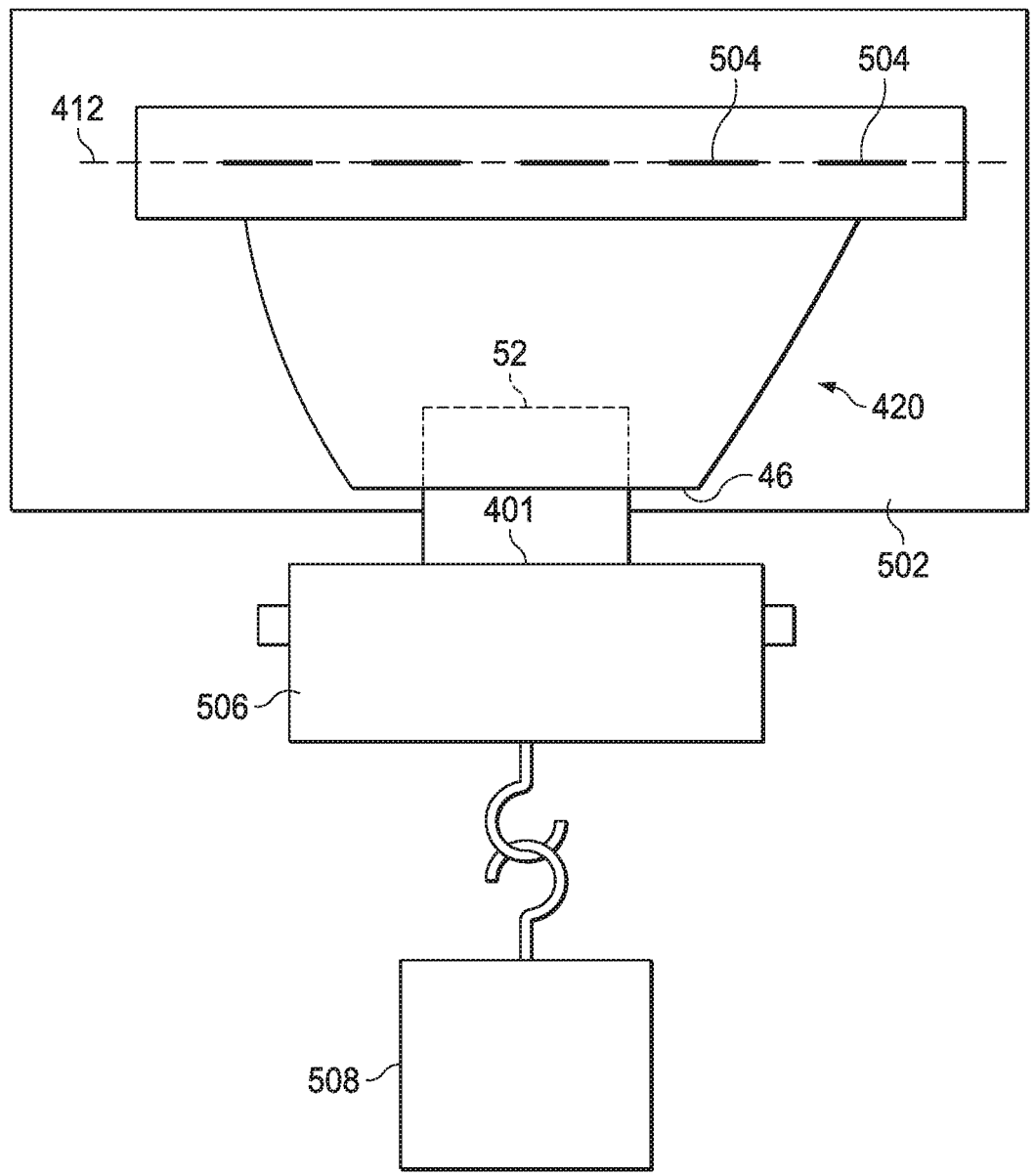

2. Referring to FIG. 5B, fix the back ear specimen 420 to a paperboard 502 with the garment-facing surface 120 facing down using, for example, one or more staples 504, along the junction line 412 to ensure that the entire length of the back ear specimen 420 is stapled without large gaps.

3. Insert the inboard edge 401 of the fastener 53 into the clamp 506.

4. Apply 2N (1N=102 gf) force to the specimen 420 in a vertical direction by clamping an appropriate weight 508 to deliver a total of 204+1 grams on the back ear specimen 420. The total of 204+1 grams of weight includes a weight of clamp 506.

5. Referring to FIG. 5C, fix the other side of the back ear specimen 420, to the paperboard 502 under the stretch condition of step 3 using, for example, one or more staples 504 to ensure that the entire length of the back ear specimen 420 is stapled without large gaps.

6. Release the clamp 506 and weight 508.

7. Determine a 4 cm×2 cm rectangle test area 424 according to below.

Figure 5D:
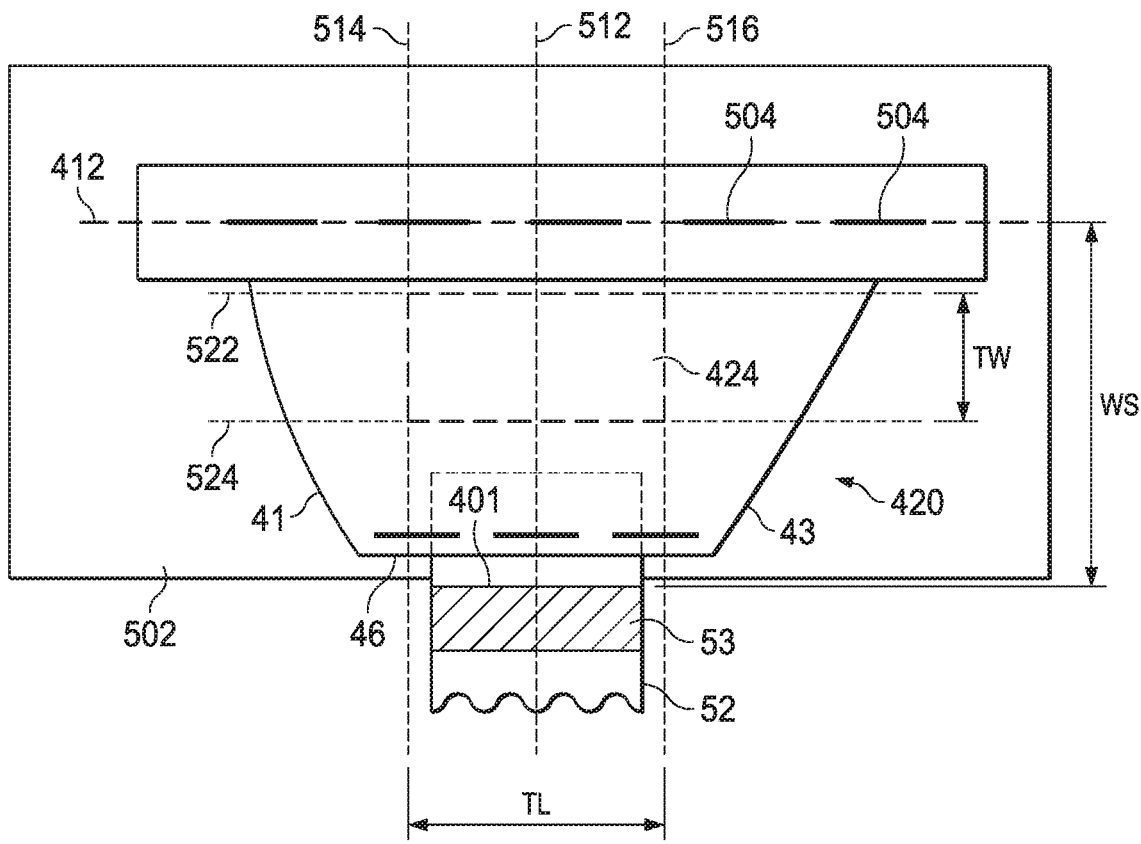

1) Referring to FIG. 5D, identify a centerline 512 of a fastener 53 parallel with a lateral axis of the diaper. Identify lines 514 and 516 parallel with the centerline 512 and 20 mm away from the centerline 512 toward a first lateral edge 41 and an opposing second lateral edge 43 of the specimen 420, respectively.

2) Identify a line 522 parallel with a longitudinal axis of the diaper and WS/10 outwardly away from the junction line 412. Identify a line 524 parallel with the line 522 and 20 mm outwardly away from 522 toward the outboard edge 46.

3) Determine a rectangle surrounded by lines 514, 516, 522 and 524 as a test area 424 having 20 mm of Tw and 40 mm of TL.

8. Capture the surface image of the test area 424 of the back ear specimen 420 with an optical profilometer such as KEYENCE 3D Measurement Macroscope VR 3200 (Keyence, JP) with a magnification of 12× under "auto stitching mode" or an equivalent mode.

9. Retrieve the surface image with a software provided by the optical profilometer and review the obtained image. Fit a reference plane by selecting the whole test area 424 identified in step 7 which means the plane that is closet to the shape of the test area is now defined as the zero height plane or reference plane. Mark five lines parallel with a lateral axis of the diaper with a length of 20 mm as sampling length across the test area to evenly divide the test area 424 to six smaller rectangular areas with a similar dimension. Set the cut-off wavelength value as $\lambda_S$=none, $\lambda_C$=20 mm, these values are parameters to eliminate short ($\lambda_S$) or long ($\lambda_C$) wavelength effects, "$\lambda_C$=20 mm" means the wavelength larger than the sampling length, 20 mm herein, will be eliminated.

10. Ra (arithmetic mean deviation of the assessed profile within the sampling length, complies with roughness definition in ISO4287:1997 3.2 Surface Texture Parameters) for each line are calculated automatically according to the equations below.

$$Ra = \frac{1}{L}\int_0^L |(x)|dx$$

Figure 6:
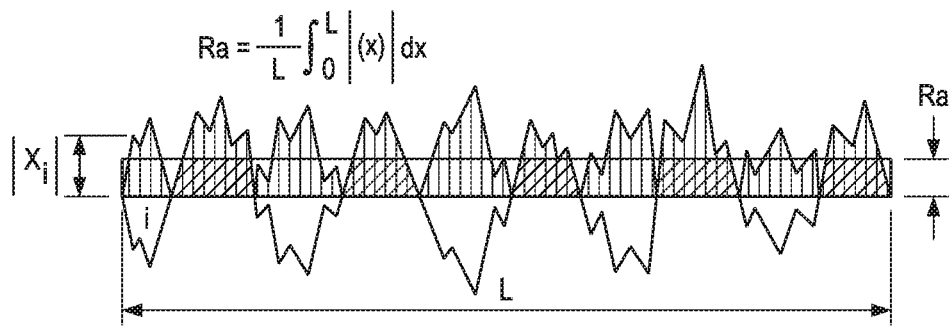
FIG. 6 is a schematic graph for Ra calculation in the Roughness Test.

Referring to FIG. 6, |Xi| is an absolute height of the profile at a point i, and L is the sampling length.

11. In like fashion, a total of five (5) replicate specimens are tested for each test product to be evaluated. Report the Ra with the mean value of the replicates.

Opacity Test

Opacity may be measured using a 0° illumination/45° detection, circumferential optical geometry, spectrophotometer such as a Spectroguide 6801 spectrophotometer (BKY Gardner, Germany). Instrument calibration and measurements are made using the standard white and black calibration plates provided by the vendor. All testing is performed in a room maintained at about 23±2° C. and about 50±5% relative humidity.

The spectrophotometer is configured for the XYZ color scale, D65 illuminant, 10° standard observer, with UV filter set to nominal. The instrument is standardized according to the manufacturer's procedures using the 1 cm view area.

1. Fix a back ear specimen to a paperboard having a 2 cm×2 cm window cut out of the center according to steps 1-3 in the Roughness Test above. The specimen should be aligned with the window such that when stretched the portion of the specimen visible through the window is centered between the LFP and LEP.

2. Place the specimen over the black plate, and place the spectrophotometer over the specimen, centered in the 2 cm window in the paperboard. The specimen should completely cover the measurement port with garment-facing surface directed toward port).

3. Press the "set" button.

4. Move the specimen and spectrophotometer to the white plate without moving the specimen's position in the measurement port, and press the "measure" button. Opacity is reported automatically. Opacities of 5 different samples per specimen are measured and the average of the 5 opacity tests is used.

EXAMPLES

Example 1: Diapers

Back Ear Material 1

Figure 4:
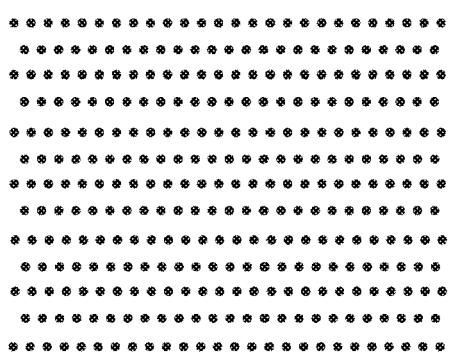
FIG. 4 is a schematic plan view of an exemplary ultrasonic bonding pattern for an elastic material for a back ear for the present invention.

Back ear material 1 including a first nonwoven and second nonwoven, and an elastomeric film sandwiched between the first and second nonwoven was prepared. Each of the first and second nonwoven were 17 gsm SMS available from Avgol, USA under tradename AVMN1048007001. The nonwovens had an average basis weight of 16.9±0.6 gsm. The elastomeric film was 40 gsm X38824 available from Tredegar Corporation, USA. The film having a width of 45 mm in a relaxed condition was stretched to 80% strain (i.e., 45 mm stretched to about 81 mm). In its stretched state, the width grew by about 3 mm due to set. While the film was stretched as described, the first and second nonwoven which were relaxed were ultrasonically bonded through the film using the bonding pattern shown in FIG. 4 and an ultrasonic bond pressure of 400N.

Back Ear Material 2

CozyFlex 2711GV (Golden Phoenix Fiberwebs, USA), an extrusion bonded laminate of nonwoven and film, was used back ear material 2.

Diaper Preparation

Diapers having back ears formed by the back ear material 1 and back ear material 2 were prepared according to a conventional diaper production process.

Example 2. Extensibility and Roughness

Table 1 shows diaper samples having back ears from various extensible materials. Back ears were cut off from the diaper samples, and extensibility of each back ear at 2N and 4N, and 4 hr growth (%) were measured according to the Back Ear Extension Test and 4 hr Growth Test, respectively. In addition, roughness of each back ear was measured according to the Roughness Test. Opacity of back ears were also measured according to the Opacity Measurement. Results are shown in Table 1 below.

TABLE 1

| Back ear material | Diaper 1 Back ear material 1 | Diaper 2 Back ear material 2 | Diaper 3*[1] | Diaper 4*[2] | Diaper 5*[3] | Diaper 6*[4] |
|---|---|---|---|---|---|---|
| WS*[5] | 73 | 74 | 76 | 82 | 63 | 57 |
| Extension at 2N (mm) | 8.1 | 7.5 | 3.4 | 4.7 | 4.2 | 6.8 |
| engineering strain at 2N | 11.1 | 10.1 | 4.5 | 5.7 | 6.7 | 11.9 |
| Extension at 4N (mm) | 27.0 | 26.1 | 10.0 | 9.1 | 6.2 | 18.7 |
| engineering strain at 4N | 37.1 | 35.3 | 13.1 | 10.9 | 9.9 | 32.7 |
| 4 hr growth (%) | 4.1 | 29.1 | 18.5 | 1.9 | 7.1 | 21.2 |
| Ra (μm) | 174 | 45 | 39 | 20 | 183 | 376 |
| Opacity at 2N | 79.84 | 71.40 | 76.60 | 47.58 | 77.56 | 69.76 |

*[1]PAMPERS 帮宝适特级棉柔 (Procter and Gamble, China)
*[2]HARGGIS 好奇银装干爽舒适 (Kimberly Clerk, China)
*[3]MERRIS (Kao, China)
*[4]MERRIS 妙而舒瞬爽透气 (Kao, China)
*[5]WS at no lateral tension load Example 3. Fitness and Stretchability Fitness and stretchability of diapers were measured using characteristics including those specified in Table 2 with 20 panels who rated the intensity of the discrete product characteristics on a 0-100 using all their senses. Data is reported as means for the entire group. Results are shown in Table 2 below.

TABLE 2

|  | Diaper 2 | Diaper 3 |
|---|---|---|
| Overall Fit (1-100) | 79 | 75 |
| Stretchiness (% JR) *[1] | 79 | 74 |

TABLE 2-continued

|  | Diaper 2 | Diaper 3 |
| --- | --- | --- |
| Overall size when applied to the baby (% JR) *[1] | 68 | 63 |
| Fit at Waist (% JR) *[1] | 79 | 74 |

(% JR) *[1]: % replying "Just Right"

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a chassis comprising a liquid pervious topsheet, a liquid impervious backsheet, an absorbent core disposed between the topsheet and backsheet;
a first and a second opposing longitudinal side edge, a front waist region and a back waist region;
a first back ear extending outwardly from the first longitudinal side edge in the back waist region;
a second back ear extending outwardly from the second longitudinal side edge in the back waist region;
wherein each of the first and second back ears comprise a laminate comprising an elastomeric film sandwiched between a first nonwoven layer and a second nonwoven layer;
wherein each of the first and second back ears has an engineering strain greater than about 8% at about or below 2N of force when measured according to the Back Ear Extension Test described herein,
wherein each of the first and second back ears have a roughness Ra lower than about 300 μm when measured according to the Roughness Test described herein.

2. The absorbent article of claim 1, wherein each of the first and second back ears has an engineering strain greater than about 10% at about or below 2N of force when measured according to the Back Ear Extension Test described herein.

3. The absorbent article of claim 1, wherein each of the first and second back ears has a roughness Ra lower than about 150 when measured according to the Roughness Test described herein.

4. The absorbent article of claim 1, wherein each of the first and second back ears has an engineering strain less than about 50% at about or below 4N of force when measured according to the Back Ear Extension Test described herein.

5. The absorbent article of claim 4, wherein each of the first and second back ears has an engineering strain less than about 40% at about 4N of force when measured according to the Back Ear Extension Test described herein.

6. The absorbent article of claim 1, wherein the laminate is an extrusion bonded laminate.

7. The absorbent article of claim 1, wherein the laminate is an ultrasonically bonded laminate.

8. The absorbent article of claim 1, wherein the laminate is void of glue.

9. The absorbent article of claim 1, wherein the laminate is a non-activated laminate.

10. The absorbent article of claim 1, wherein each of the first and second back ears have about 1% to about 20% of a 4 hr growth when measured according to the 4 hr Growth Test described herein.

11. The absorbent article of claim 1, wherein the first and second back ears have an opacity of at least 70 when measured according to the Opacity Test described herein.

12. The absorbent article of claim 1, wherein the first and second back ears are joined to at least one component of the chassis.

13. The absorbent article of claim 1, wherein the first and second back ears are integral with the chassis.

14. The absorbent article of claim 1, wherein at least one back ear comprises an extension of at least about 10 mm at about or below 2N of force when measured according to the Back Ear Extension Test described herein.

15. An absorbent article comprising
a chassis comprising a liquid pervious topsheet, a liquid impervious backsheet,
an absorbent core disposed between the topsheet and backsheet;
first and second opposing longitudinal side edges, a front waist region and a back waist region;
a first back ear extending outwardly from the first longitudinal side edge in the back waist region;
a second back ear extending outwardly from the second longitudinal side edge in the back waist region;
wherein each of the first and second back ears comprise a laminate having an elastomeric film sandwiched between a first nonwoven layer and a second nonwoven layer;
wherein each of the first and second back ears has an engineering strain greater than about 8% at about or below 2N of force when measured according to the Back Ear Extension Test described herein, and
wherein each of the first and second back ears have about 1% to about 20% of a 4 hr growth when measured according to the 4 hr Growth Test described herein.

16. An absorbent article comprising:
a chassis comprising a liquid pervious topsheet, a liquid impervious backsheet, an absorbent core disposed between the topsheet and backsheet;
first and second opposing longitudinal side edges, a front waist region and a back waist region;
a first back ear extending outwardly from the first longitudinal side edge in the back waist region;
a second back ear extending outwardly from the second longitudinal side edge in the back waist region;

wherein each of the first and second back ears comprise a laminate comprising an elastomeric film sandwiched between a first nonwoven layer and a second nonwoven layer;

wherein at least one of the first and second back ears has an extension of at least about 10 mm at about or below 2N of force when measured according to the Back Ear Extension Test described herein, wherein at least one of the first and second back ears has about 1% to about 20% of a 4 hr growth when measured according to the 4 hr Growth Test described herein.

17. The absorbent article of claim 16 wherein the at least one of the first and second back ears comprises an extension of at least about 20 mm at about or below 4N of force.

18. The absorbent article of claim 16 the at least one of the first and second back ears comprises a non-activated laminate.

19. The absorbent article of claim 16, wherein the at least one of the first and second back ears have an opacity of at least 70 when measured according to the Opacity Test described herein.

20. The absorbent article of claim 16, wherein the elastomeric film is of smaller size than the first nonwoven and second nonwoven layers.

21. The absorbent article of claim 1, wherein the laminate comprises a single elastomeric film sandwiched between a single first non-woven layer and a single second non-woven layer that extend in a longitudinal direction from a first lateral edge to a second lateral edge of each of the first and second back ears.

22. The absorbent article of claim 1, wherein the chassis is defined by a longitudinal centerline and a lateral centerline that is orthogonal to the longitudinal centerline and wherein the elastomeric film is extendable in a lateral direction that is parallel to the lateral centerline.

* * * * *